United States Patent [19]

Hamann

[11] Patent Number: 5,133,392
[45] Date of Patent: Jul. 28, 1992

[54] LIQUID INJECTION USING CONTAINER BOTTOM SENSING

[75] Inventor: J. Eric Hamann, Rochester, Gregory M. Keyes, Lima, both of N.Y.

[73] Assignee: Eastman Kodak Company, Rochester, N.Y.

[21] Appl. No.: 683,384

[22] Filed: Apr. 10, 1991

[51] Int. Cl.⁵ .............................. B65B 1/04; B01L 3/02
[52] U.S. Cl. .................................... 141/1; 141/9; 141/263; 73/864.025
[58] Field of Search ............... 141/1, 4, 5, 9, 263, 141/375, 104, 83; 116/227; 73/864.14, 864.15, 864.25, 863.01, 863.21, 301, 290, 302; 222/1, 56

[56] References Cited

U.S. PATENT DOCUMENTS

| | | | |
|---|---|---|---|
| 2,648,476 | 8/1953 | Kennedy | 141/1 |
| 2,771,913 | 11/1956 | Flasnocker | 141/9 |
| 3,311,263 | 3/1967 | Harmon | 222/1 |
| 3,894,438 | 7/1975 | Ginsberg | 73/863.01 |
| 4,539,855 | 9/1985 | Jacobs | 73/864.25 |
| 4,574,850 | 7/1986 | Davis | 141/9 |
| 4,577,514 | 3/1986 | Bradley et al. | 73/863.01 |
| 4,675,301 | 6/1987 | Chauneski et al. | 73/863.01 |
| 4,777,832 | 10/1988 | Prodosmo et al. | 73/863.02 |
| 4,780,833 | 10/1988 | Atake | 73/864.14 |
| 4,790,183 | 12/1988 | Pfost et al. | 73/290 V |
| 4,794,085 | 12/1988 | Jessop et al. | 436/54 |
| 5,015,591 | 5/1991 | Meyrat et al. | 73/864.25 |
| 5,022,556 | 6/1991 | Dency et al. | 222/1 |

FOREIGN PATENT DOCUMENTS

0223758  5/1987  European Pat. Off.

*Primary Examiner*—Henry J. Recla
*Assistant Examiner*—David J. Walczak
*Attorney, Agent, or Firm*—Dana M. Schmidt

[57] ABSTRACT

There is disclosed a method for injecting liquid into a container that senses the location of the bottom of the container, not simply by the force of "running into" the container, but rather, by first sealing the dispensing orifice against the bottom of the container, pressuring the liquid in the orifice and then backing off the orifice until release of liquid out the orifice is sensed.

4 Claims, 4 Drawing Sheets

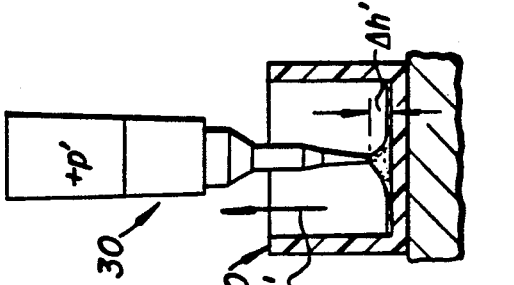
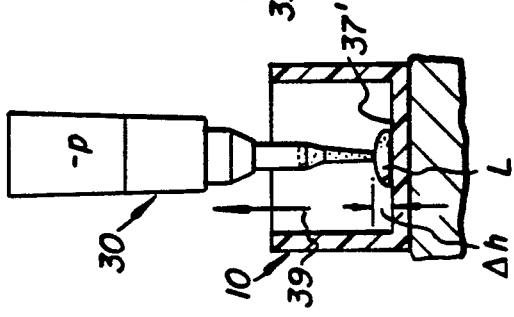
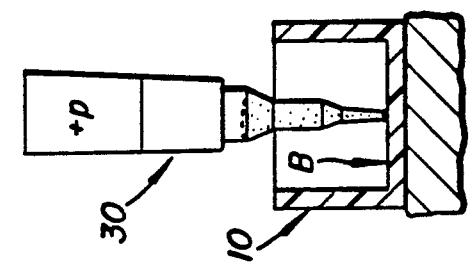
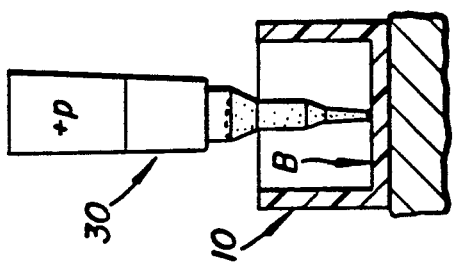
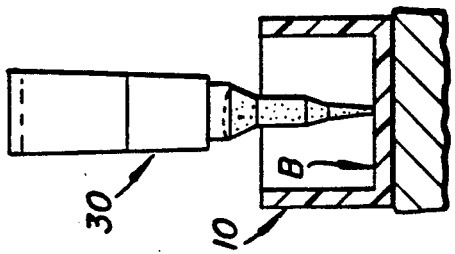
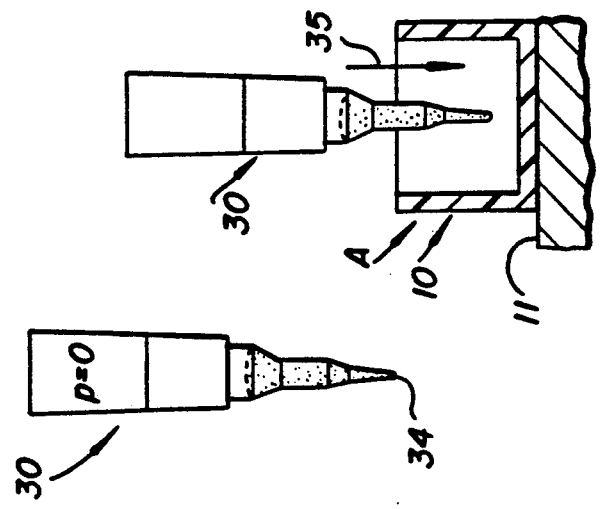

LIQUID INJECTION USING CONTAINER BOTTOM SENSING

FIELD OF THE INVENTION

The invention is directed to a method of dispensing liquid into a container, and especially, a method for automatically achieving optimal spacing for such dispensing by the use of pressure feedback.

BACKGROUND OF THE INVENTION

In some instances in the clinical analysis of blood samples, it is desirable that the patient sample be diluted so as to retest an out-of-range condition. By adding the sample to a diluent, or vice versa, in a predetermined ratio, e.g., 1:1, the out-of-range value is reduced to a within-range reading. For example, the condition can occur in assays for glucose.

Prior art approaches have been to eject the sample or the diluent into an empty container until the desired volume is achieved, and then the other liquid is added. In most, if not all of such approaches, no care is given to the location of the bottom of the container. The dispenser tip should not be unduly submerged during liquid ejection, lest substantial amounts of the liquid end up on the surface of the withdrawn tip instead of inside the container. Hence, most such approaches err on the side of spacing the tip so high above the bottom surface of the container that the liquid is ejected in drops, rather than a continuous stream. That is, the distance is too great to allow a continuous stream to flow.

Ejection as drops produces no problem, until the last amount of liquid is ejected. That last amount tends to hang as a pendant drop, with or without perfusion up the outside surface of the dispensing tip. We have discovered that as much as 25% of the desired volume can end up in such a pendant drop, rather than in the liquid in the container, so that the dilution ratio inside the container can be severely altered. Such a dilution method is unacceptable.

This invention is not the first to appreciate the importance in knowing where the bottom of the receiving container actually is, in each instance. European Patent Publication 223,758 teaches the sensing of the bottom of each container, simply by measuring the increase in axial force on the pipette that occurs when it strikes the bottom. However, this is subject to error. For example, if the pipette strikes a side wall or side wall projection of the container before reaching bottom, an axial component of force can still be delivered. This is particularly a problem for non-cylindrical containers or those with sloping side walls. The result in such case can be a false reading of bottoming. Thus, the technique used by this European application places an undue premium on proper location of the dispenser tip in the X-Y plane, vis-a-vis the container, to avoid side wall contact. Otherwise, the technique of that application will not in fact always determine the actual bottom. Still further, the axial force on the pipette is measured by this technique using a sensor added only for this purpose. A better technique would use sensors already in place.

SUMMARY OF THE INVENTION

We have developed a bottom-sensing method that solves the above-mentioned problems.

More specifically, there is provided a method for injecting liquid into a container from a dispenser orifice moved vertically relative to the container by moving means in response to control means and sensing means, the orifice being resiliently mounted in the vertical direction, the method including the steps of moving the orifice vertically towards the bottom of the container, sensing the bottom, and thereafter injecting liquid into the container. The method is improved in that the moving step comprises moving the orifice to a sealing location beyond the nominal location of the container bottom so that the orifice is sealed by the bottom, and the sensing step comprises the steps of a) actuating the pressure means while the orifice is sealed by a vertical force at the sealing location, b) slowly withdrawing the vertical force on the orifice from the container bottom while sensing the pressure on the liquid in the orifice, c) detecting a decrease in the pressure when the orifice is no longer sealed against the container bottom and liquid starts to be ejected from the orifice by the pressure means, and d) generating a signal in response to step c) that identifies the location of the unsealed orifice as being at the "bottom".

Therefore, it is an advantageous feature of the invention that the actual bottom, rather than side walls, of each container into which liquid is injected, is sensed to allow proper and complete dispensing of the liquid to be received by the container.

It is another advantageous feature of the invention that a method is provided for injecting liquid into a container from a dispenser that insures, for each container, that all of the liquid ejected from the dispenser is in fact received in the container and is not left on the dispenser.

It is a related advantageous feature of the invention that such a method of injecting liquid is provided that locates the dispenser of the liquid so that a continuous stream of liquid is provided into the container.

Other advantageous features will become apparent upon reference to the following Description of the Preferred Embodiments, when read in light of the attached drawings.

BRIEF DESCRIPTION OF THE DRAWINGS

FIGS. 2A–2F are elevational views similar to FIGS. 1A and 1B but illustrating the practice of the invention;

DESCRIPTION OF THE PREFERRED EMBODIMENTS

The invention is hereinafter described in the context of the preferred embodiments, wherein certain preferred dispensing tips are used in a preferred analyzer to dispense liquid, most preferably, patient sample or diluent, into preferred containers in an analyzer such as the type manufactured under the tradename "Ektachem 700" or "Ektachem 250" by Eastman Kodak Company. In addition, the invention is useful regardless of the liquid being dispensed, and the kind of dispensing tip or analyzer that is used. Any container can be used to receive the liquid provided its bottom surface will seal against the dispenser orifice.

Figure 1A:
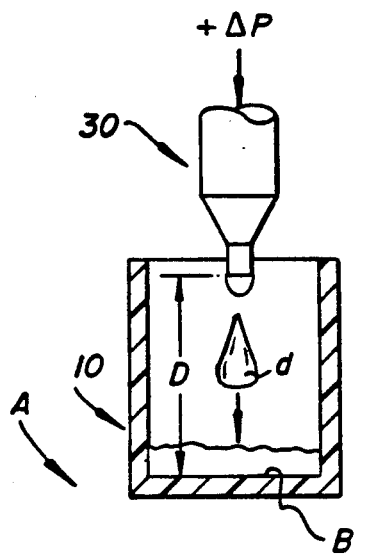
FIGS. 1A and 1B are partially sectioned, elevational views illustrating a prior art method of injecting liquid into a container.
Figure 1B:
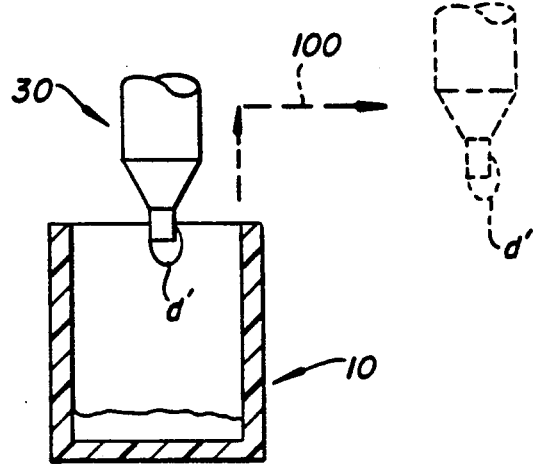

The problem addressed by this invention is illustrated in FIGS. 1A and 1B. That is, a container 10 is located at a station A, to receive a liquid, such as a diluent, from a conventional disposable tip 30, mounted on a dispenser (not shown). To avoid erring on inserting the tip too far into the container so as to ram the tip into the bottom, the analyzer is programmed to err on the "high side", that is, to locate tip 30 an excessive distance "D" above the bottom surface B of container 10. Distance "D" in many cases is too great to allow the injected liquid to pass as a stream—instead, it passes a drops "d", when a pressure increase+ΔP is provided, FIG. 1A. However, FIG. 1B, the last drop d' is often too small to ensure that it will fall into container 10. Instead, it hangs from tip 30 as a drop d', so that it leaves with the tip (arrow 100) (shown in phantom), thus destroying the expected dilution ratio when the patient sample is next injected into the diluent already in the container. That is, the volume of drop d' can be up to 25% of the volume expected to be injected into container 10, which clearly alters the expected dilution ratio.

Figure 3:
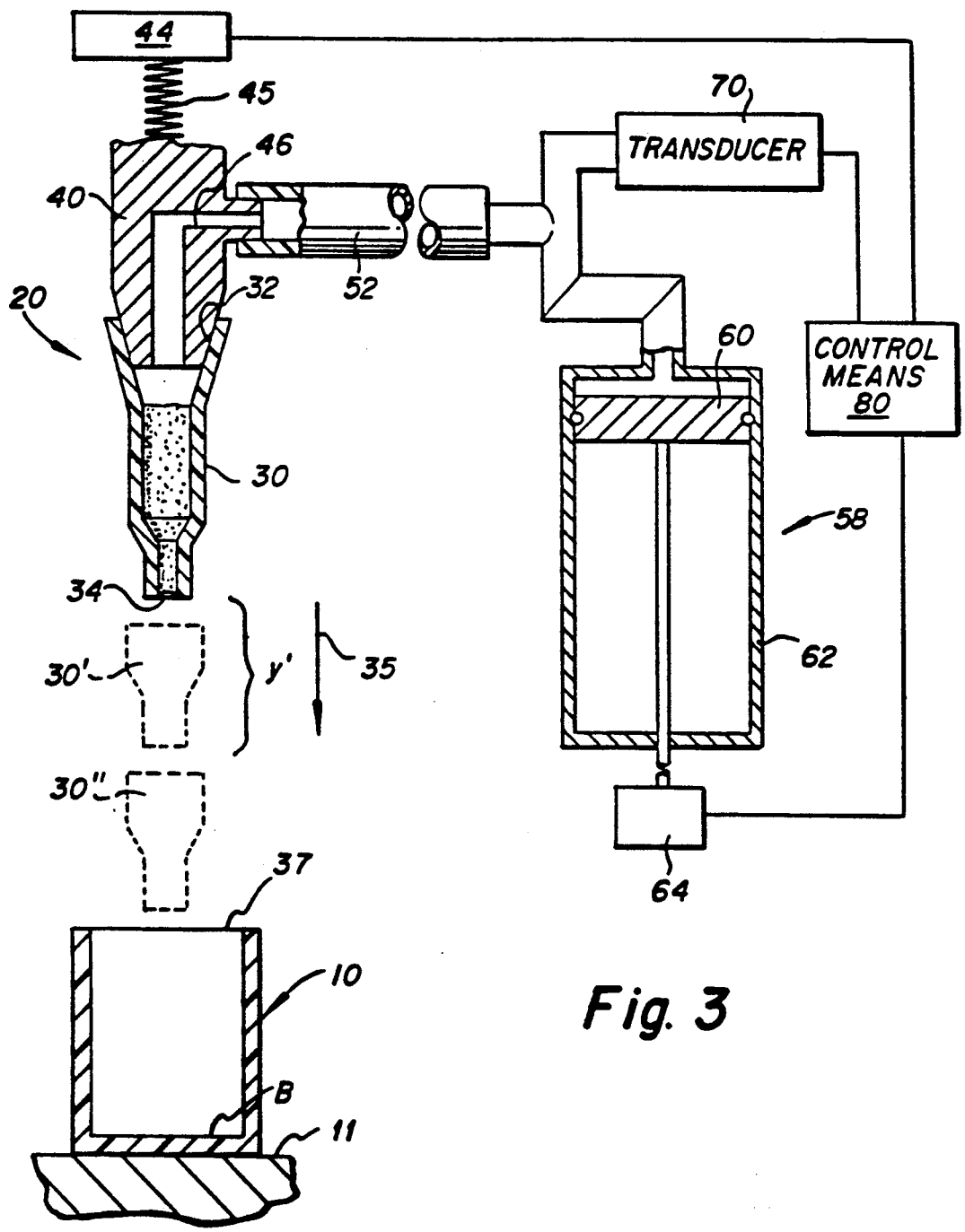
FIG. 3 is a partially schematic fragmentary elevational view of apparatus useful in the invention.

The method of the invention is best understood from FIGS. 2A-2F, using apparatus such as the apparatus shown in FIG. 3. That is, a dispenser (not shown in FIGS. 2A-2F) has a disposable tip 30 mounted thereon with a dispense aperture 34, the tip being of any convenient type. (Tips available under the tradename "Ektachem 700" disposable tips from Eastman Kodak Company are useful.) At a suitable aspirating station, such a tip is filled with an appropriate volume of the liquid having the smaller volume in the mixture, e.g., the sample or a diluent such as 10 $\mu$L of water or 7% bovine serum albumin, plus a "dead" volume, for example, 20 $\mu$L, and following aspiration, the pressure inside tip 30 is essentially equal to atmospheric (FIG. 2A). Next, the tip is placed vertically over a container, not shown, which is the condition illustrated in FIG. 2A. Thereafter, relative movement, arrow 35, is provided between tip 30 and container 10, FIG. 2B. Such relative movement is maintained (preferably by moving tip 30 down towards container 10 fixed on a support 11), until tip 30 seals against bottom surface B, FIG. 2C. The dispenser is conventionally constructed to be slightly resilient in at least the vertical direction, thus allowing sufficient over-travel of tip 30 downward against surface B to apply a vertical force without damaging the container or the dispenser, and yet still sealing tip orifice 34 against surface B.

At this point, FIG. 2D, the pressure inside tip 30 is increased by an amount +p and the pressure inside tip 30 is monitored by a sensing means. The amount "+p" is that amount just sufficient to eject a meniscus from tip 30 if the tip is not sealed. Thereafter, tip 30 is withdrawn in increments, until enough of the resilient pressure has been withdrawn, shown as distance Δh, FIG. 2E, as to cause tip 30 to unseat and some of the liquid (L) to be ejected onto surface B.

The amount of meniscus that is ejected by pressure increase "+p" depends on the tip geometry, primarily. In one example, the pressure +p caused ejection of about 5 $\mu$L of the liquid, but other amounts can be used. Importantly, while the liquid is ejected, FIG. 2E, a pressure decrease −p is registered by the sensing means, and this decrease is used to trigger that the "bottom" (here, surface B) of the container has been reached. This position, shown in FIG. 2E, is stored in memory as the "bottom" position.

Thereafter, while tip 30 is withdrawn at a prescribed rate, a new +p' pressure is applied to tip 30 to eject the remaining aliquot of the liquid to be dispensed into this container. That is, the new, changing height Δh' of tip 30 above surface B is selected so as to continue to maintain the ejection of the liquid as a continuous stream, FIG. 2F. (Although FIG. 2F shows all of the contents of tip 30 being ejected, preferably the above-mentioned dead volume remains.)

Then, when tip 30 is totally withdrawn (not shown), the total distance the dispenser has moved from the tip position shown in FIG. 2E is recalled. Thus, knowing the location of surface B as sensed in FIG. 2E, the dispenser can re-enter container 10 with a new tip bearing the other liquid of the mixture, and properly locate the new tip at that surface for dispensing the proper aliquot of the other liquid in the manner shown in FIG. 2F. That is, knowing where bottom surface B is, the dispenser "knows" where the top of the first liquid is and hence where the new tip should be to dispense the second liquid as a continuous stream. (Conventional software is used to provide such calculations.)

By way of example, Δh of FIG. 2E, when liquid L releases out of tip 30 due to the unseating of the tip, can be about 0.20 mm. The withdrawal of the tip as shown in FIG. 2F proceeds with a dispensing pressure sufficient to dispense at a rate of, e.g., 100 $\mu$L/sec.

Suitable analyzer apparatus 20 for carrying out the steps of FIGS. 2A-2F is shown in FIG. 3. Such an analyzer uses conventional parts, heretofore known as shown for example in U.S. Pat. No. 4,794,085. That is, a tip 30 is removably mounted at its larger aperture 32 onto an aspirator/dispenser probe 40. Probe 40 is moved relative to a container 10 suitably supported at 11. That is, probe 40 is moved preferably up and down, by a conventional drive 44. A spring 45 disposed between drive 44 and probe 40 represents the compliancy that allows the drive to "overdrive" tip 30 into container 10 without damage. Probe 40 has an internal passageway 46 connected to a pressure transducer 70 via a hose 52, and also to means 58 for altering the pressure inside tip 30. (Such means 58 comprise, e.g., a piston 60 moved inside a cylinder 62 by a drive means 64, between the various positions shown in phantom.) Control means 80 is used to detect the pressure signal generated by transducer 70, and in turn acts upon both drive means 44 and 64 in accordance with an appropriate program to control the movement and pressure, respectively, of tip 30. Control means 80 is preferably a microcomputer in analyzer, and transducer 70 is one having a high sensitivity, low internal air volume and high stability, for example, a piezoelectric transducer.

Movement of tip 30, arrow 35, is in increments, so that aperture 34 moves first a distance Y' to the phantom position 30', and then to phantom position 30", and so forth, until the tip has sealed against bottom surface B, also as shown in FIG. 2C. A nominal location of surface B can be predicted by a single dry run prior to use, to avoid driving tip 30 too far down against container 10, beyond the resiliency that is built into probe 40. At this time, an increase in pressure of +p is provided by an advance of piston 60 within cylinder 62, to test for the unseating of tip 30 from bottom surface B. As force on tip 30 is incrementally reduced by drive 44, through the release of spring 45, the pressure inside tip 30 is monitored by transducer 70 plus control means 80, to detect when a sudden decrease occurs that is indicative of the tip becoming unsealed from surface B.

It will be readily appreciated that a threshold signal is set, beyond which the pressure must decrease in amount in order to represent the unsealing of tip 30. For example, if the +p pressure that is used to test for unsealing generates a signal of about 450 mV, then a useful threshold value is about 390 mV, where the transducer produces about 300 mV per 2.54 cm of $H_2O$ pressure.

Figure 4:
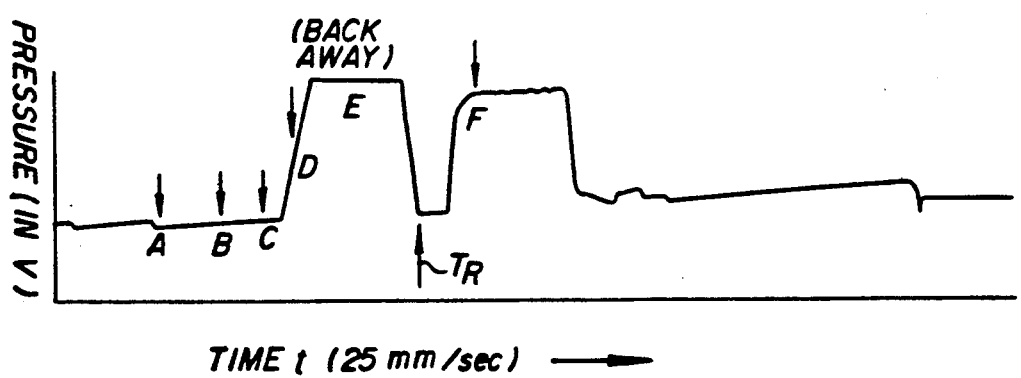
FIG. 4 is a pressure profile of the change in pressure that occurs during the process illustrated by FIGS. 2D and 2E.

Such a threshold is shown in FIG. 4, where a pressure descrease of about 400 mV occurs at time $T=T_R$, when unsealing first occurs. The remainder of the events shown in FIG. 4 are as follows: at time t corresponding to point A, liquid is already within the dispensing tip. At time t corresponding to point C, the tip is sealed on the bottom. From point C during the time at point D, +p pressure has been applied by the pump (also shown in FIG. 2D). The plateau during point E represents the time when the downward vertical force on the tip is gradually reduced (marked "back away"). The pressure drop at $T_R$ represents the unsealing event, and the tip location at this time is "marked". Finally, the pressure rise to point F represents the dispensing of the remainder of the liquid into the container, FIG. 2F.

Figure 5:
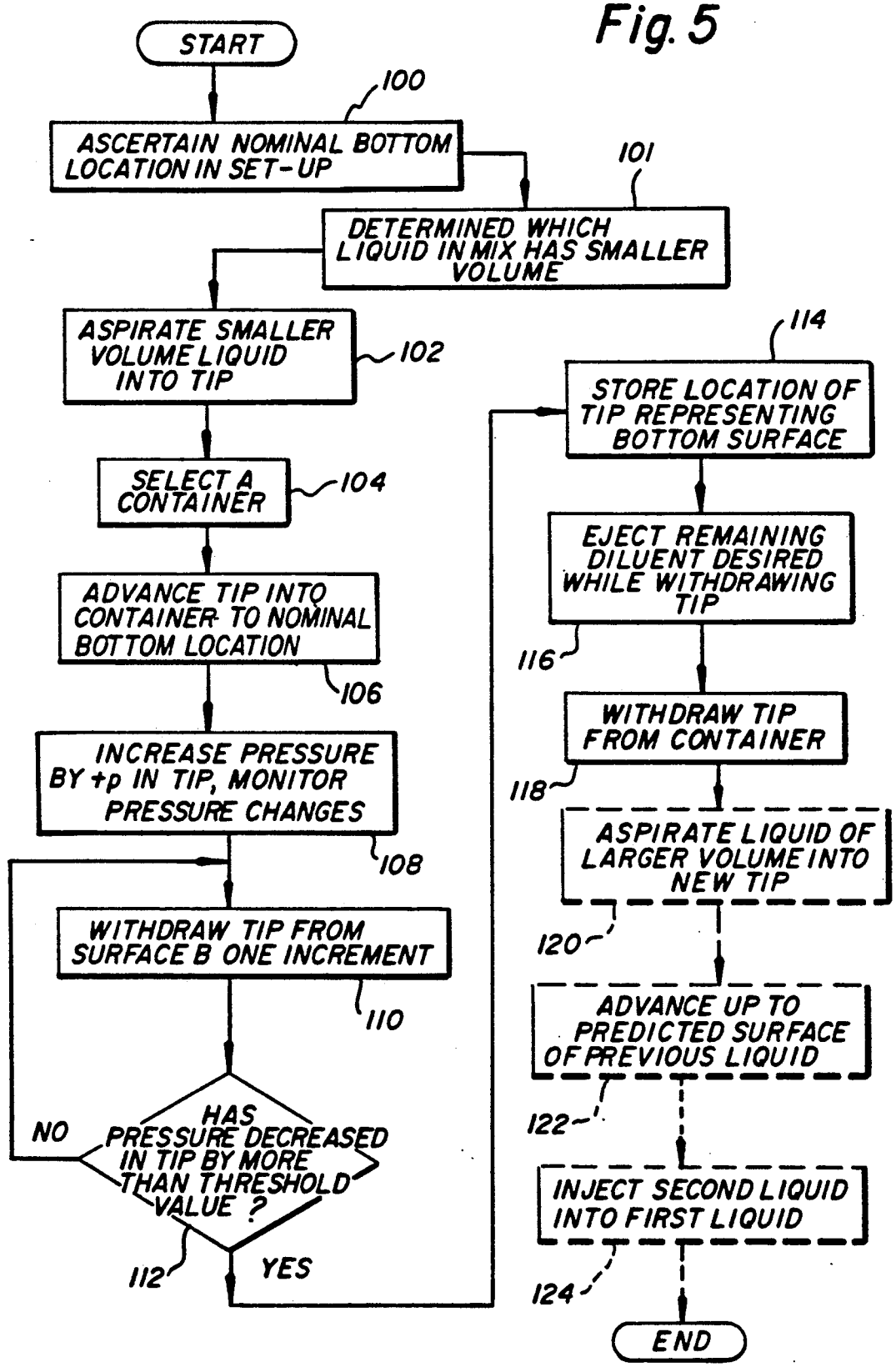
FIG. 5 is a flow chart illustrating the steps that are followed in programming an analyzer to carry out the method of the invention.

Any suitable program can be used in a conventional manner to program control means 80. The flow chart of FIG. 5 is illustrative of the steps of the computing process involved. The process requires, first, that the manual location of bottom surface B be ascertained, step 100, as noted above, to prevent damaging over-travel of the dispenser proble. Next, step 101, the liquid which represents the smaller of the two volumes in the mixture is determined, and it is this liquid, step 102, that is aspirated into a tip 30 on the dispenser. Thereafter tip 30 is advanced into a selected container, step 104, until aperture 34 reaches the nominal location of the bottom surface, where it should seal against bottom surface B, step 106, as determined from step 100.

At this point, the pressure means, namely the piston of the dispenser, is advanced an amount +p, step 108, while the pressure is monitored via the transducer (70 in FIG. 3). This accomplishes two things: it confirms that indeed the tip is sealed. Also, it allows tip 30 to be thereafter withdrawn a selected single increment, step 110, which for example can be six half-steps if drive 44 of FIG. 3 is a stepper motor. Control means 80 then queries, step 112, whether the pressure in tip 30 has decreased more than the selected threshold. If not, step 110 is iterated until the query is answered positively, step 114. At this point, the "location", i.e., the position of drive 44, is stored in memory, and the pressurizing means is actuated to generate a +p' to further eject the remaining amount of the desired aliquot of diluent, step 116, while tip 30 is incremented backwards by drive 44 at a prescribed rate.

Finally, tip 30 is withdrawn from the container, step 118.

Thereafter, as a further option, a new tip is provided with the liquid having the larger volume in the mixture, step 120, the tip is advanced to the predicted location of the liquid surface previously deposited, step 122, as determined by step 114, and the second liquid is injected into the first, step 124. Steps 120-124 are considered optional, since once the first liquid is in place, other steps can be followed with respect to that liquid or even in properly locating a new tip with the second liquid, relative to the surface of the first liquid.

The invention has been described in detail with particular reference to certain preferred embodiments thereof, but it will be understood that variations and modifications can be effected within the spirit and scope of the invention.

What is claimed is:

1. In a method for injecting liquid into a container from a dispenser orifice moved vertically relative to said container by moving means in response to control means and sensing means, said orifice being resiliently mounted in the vertical direction, the method including the steps of moving said orifice vertically towards the bottom of said container, sensing said bottom, and thereafter injecting liquid into the container;

the improvement wherein said moving step comprises moving said orifice to a sealing location beyond a nominal location of said container bottom so that said orifice is sealed by said bottom, and said sensing step comprises the steps of a) actuating said pressure means while said orifice is sealed by a vertical force at said sealing location, b) slowly withdrawing said vertical force on said orifice from said container bottom while sensing the pressure on the liquid in said orifice, c) detecting a decrease in said pressure when said orifice is no longer sealed against said container bottom and liquid starts to be ejected from said orifice by said pressure means, and d) generating a signal in response to said step c) that identifies the location of said unsealed orifice as being at the "bottom", whereby all the liquid to be dispensed actually leaves said dispenser.

2. A method as defined in claim 1, wherein said step d) further includes e) labeling the location of the unsealed orifice as the "bottom" location; and further including the step of thereafter continuing the injection of liquid into the container while withdrawing said orifice from said flexible container bottom and tracking the distance traveled away from said "bottom" location.

3. A method as described in claim 1, wherein said dispenser orifice is part of a clinical analyzer and said liquid is a diluent for a patient sample.

4. A method as described in claim 2, wherein said dispenser orifice is part of a clinical analyzer and said liquid is a diluent for a patient sample.

* * * * *